US00PP07929P

United States Patent [19]

Rother

[11] Patent Number: Plant 7,929

[45] Date of Patent: Aug. 4, 1992

[54] *SCAEVOLA AEMULA* PLANT NAMED BLUE WONDER

[75] Inventor: Reinhard W. Rother, Emerald, Australia

[73] Assignee: Kientzler KG, Gensingen, Fed. Rep. of Germany

[21] Appl. No.: 644,633

[22] Filed: Jan. 23, 1991

[51] Int. Cl.[5] ..... A01H 5/00

[52] U.S. Cl. ..... Plt./68.1

[58] Field of Search ..... Plt./68

*Primary Examiner*—James R. Feyrer

*Attorney, Agent, or Firm*—Foley & Lardner

[57] ABSTRACT

A *Scaevola aemula* cultivar named Blue Wonder, having large, dark green leaves, intensely colored violet-blue flowers, simultaneous flowering on each stem and an overall superior branching habit.

2 Drawing Sheets

The present invention relates to a new and distinctive cultivar of *Scaevola aemula*, known by its cultivar name Blue Wonder. The species is native to Australia.

Varieties of *Scaevola aemula* have proven good garden plants, able to prosper in normal conditions. They are particularly popular as border plants. The plant produces four months or more of flowering, and tolerates a high degree of climatic and soil variations.

The species is decumbent, with soft leaves and stems. Cut flowers of the species remain upstanding and rigid for as long as two weeks. Plants of the species grown in full sun exhibit vigorous and floriferous characteristics, although the solid should be kept reasonably moist to achieve best results.

The habit and form of the species is quite variable. All forms, however, have fan-shaped flowers which bloom in spring and summer, with the flowers varying greatly in size. Flower color is normally mauve to blue, although other colors do exist. The leaves are normally bright green. It is an attractive potted or garden plant, with its tendency to cascade. The native Australian species is popularly known as the Fairy Fan Flower.

Blue Wonder was selected by applicant from the seedling progeny from a cross of unknown parents of *Scaevola aemula* by applicant, at the Outeniqua Nursery, Emerald, Victoria, Australia. Subsequent asexual propagation by applicant over successive generations has shown that the unique features of this new cultivar are carried over to successive generations. Asexual propagation can be by cuttings or by tissue culture.

Blue Wonder has not been observed under all possible environmental conditions. The phenotype may vary significantly with variations in environment, such as temperature, light intensity, soil conditions, nutrients applied and length of day. For example, under hot, shady conditions the flower color becomes relatively pale, while under cool and bright conditions the flower color is more bright and intense.

The following characteristics in combination distinguish Blue Wonder from other cultivars of the same species found in the wild:

1. Its vigorous habit, producing a larger and more attractive plant.
2. The leaves are larger and darker green.
3. The flowers are larger and more intense in color.
4. More flowers are produced simultaneously per stem.
5. Its overall superior branching habit.

6. Its blue violet flower color.

Blue Wonder is readily distinguishable from the closest known cultivars of the species. The cultivar White Form is much smaller and possesses less succulent foliage. It flowers less profusely than does Blue Wonder, and its individual flowers are smaller and pure white.

The cultivar Gawler-Ras has even smaller and narrower foliage than does White Form. Gawler-Ras is further characterized by weak growth, sparse branching and lilac-purple flowers of about half the size of Blue Wonder.

In comparison to its parents, Blue Wonder is superior in several respects. In fact, in view of the obvious improvements regarding Blue Wonder, the parents were subsequently discarded.

In the accompanying color photographic drawings Sheet 1 depicts a flowering stem of *Scaevola aemula* in its wild form beside a specimen of the cultivar Blue Wonder.

Sheet 2 is a perspective view of Blue Wonder, depicting its overall appearance. The colors in these photographs are as true as is possible to obtain in a color reproduction of this type, but the flower color does not correspond to the true flower color correctly expressed below by color value. The photographic color is more reddish in tone than the true bluish violet flower color of Blue Wonder.

Color references are made to the Royal Horticultural Society Colour Chart except where general terms of ordinary dictionary significance are used.

Growth habit: The cultivar is monopodial, perennial and herbaceous.

Stems:

*Shape, size and other features.*—The stems are semi-upright, prostrate or semi pendulous. The stem tips are more or less vertical. Stem diameters vary from 2–4 mm, with lengths up to 1,000 mm. The stems are not hollow, but contain a whitish pith zone. Stems are slightly keeled, smooth and non-pubescent.

*Color.*—The stems are olive green to reddish brown.

*Branching habit.*—Auxiliary branching from non-flowering leaf axils; branching increases from the stem tip to the base of the plant. The leaf axils on the flowering stems do not produce axillary shoots.

Foliage:

*Shape in general.*—The leaf shape is more or less spatulate, and the leaf margins are slightly to strongly serrated.

*Color.*—Upper leaf surface is dark olive-green and the lower surface is light green. Both surfaces are slightly pubescent.

*Size and shape.*—Strong heterophyllic tendencies; leaves on vegetative stems are relatively large and long (60–150 mm long, 15–50 mm wide), with strongly serrated margins. Leaves on flowering stems are smaller (15–40 mm long, approximately 10 mm wide). The smaller leaves are only slightly indented, shallowly serrate or entire. The leaf form is generally ovate-acuminate. Leaf shape and size can vary greatly, depending on growing conditions, light intensity and length of day.

*Other features.*—Older leaves are more or less succulent. Phyllotaxis more or less spiral, especially on the flowering portions of the stems. Internode length is highly variable; the internodes being longer (20–50 mm) on the non-flowering portions of stems than on the flowering portions (5–30 mm).

Flowers:

*Shape.*—Flower is fan-shaped.

*General.*—Flowers appear on the leaf axils of flowering stems, one flower per axil; sessile and without a recognizable flower stem, with two adjacent lanceolate leaflets approximately 10 mm in length. Flower is zygomorphous. Ovary is green, elongate-ovate in shape and about 3 mm in length.

*Flower throat.*—Open along the upper side, exposing the anthers and stigma, about 15 mm long, yellow with purple stripes along the edges and in the perianth region.

*Perianth.*—Violet blue, approximately 88B (substantially more blue than shown in photographs). The lower surface is lighter blue with whitish wedges. Diameter of the perianth is 25–30 mm, the perianth being flat and at an obtuse angle to the throat. The perianth is semi-circular fan-shaped, and is made up of five acuminate-ovate petals fused at their bases to form the throat.

*Petal tips.*—Acuminate.

*Anthers.*—1–2 mm long, first yellow, then brownish. Filaments are 3–4 mm long, and protrude from the throat.

*Pistils.*—About 15 mm long, slightly bent, purple upper surface and greenish lower surface. The pistil is broad, covered with 2 mm purplish hairs, and the yellowish white tip is bent downwards. In most cases, 5–15 flowers are open on each stem tip simultaneously. As the flower fades, it falls off altogether with the pistil.

Fruit: The fruit is oval-elongated, about 4–5 mm in length, greenish-purple, located in the leaf axils and sessile. One seed is produced per fruit, which is about 3–4 mm in length, blackish-brown and surrounded by a succulent endocarp. Seeds do not permit true to type propagation.

I claim:

1. A new and distinct cultivar of *Scaevola aemula* named Blue Wonder, as illustrated and described.

* * * * *

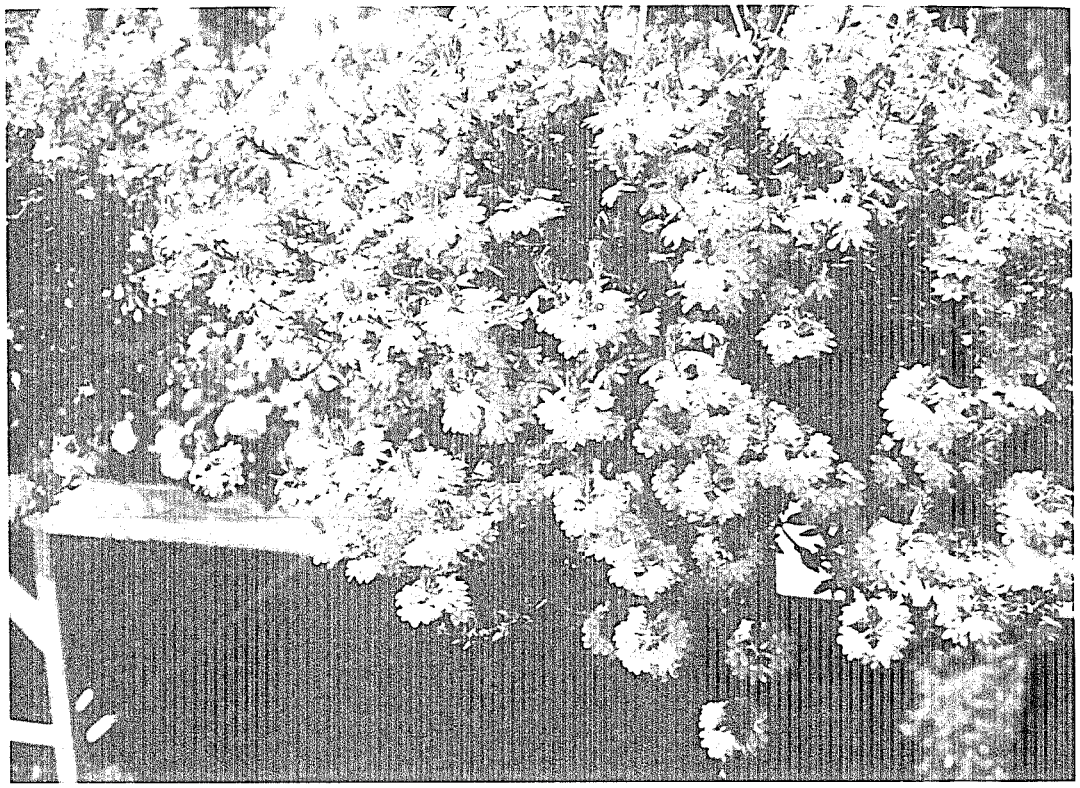

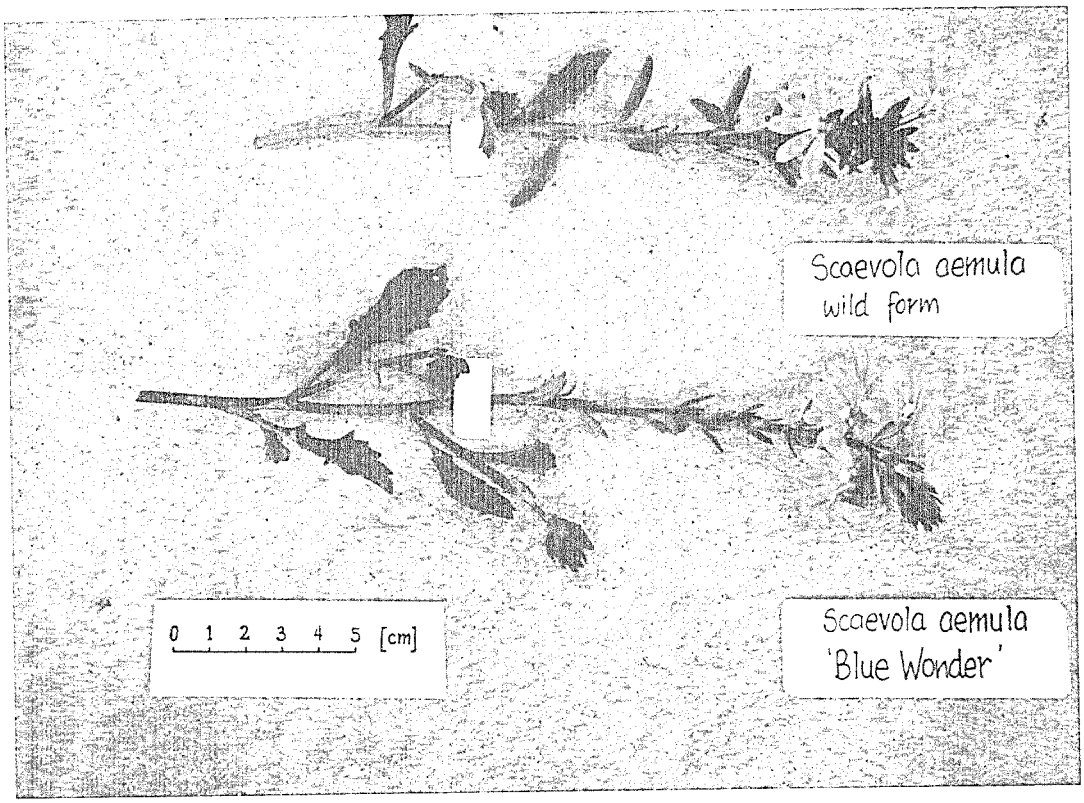
Scaevola aemula
wild form
0 1 2 3 4 5 [cm]
Scaevola aemula
'Blue Wonder'